US012774285B2

(12) United States Patent
Huntley

(10) Patent No.: US 12,774,285 B2
(45) Date of Patent: Oct. 27, 2026

(54) PROCESS FOR PURIFYING NOROXYMORPHONE

(71) Applicant: KNOA PHARMA LLC, Stamford, CT (US)

(72) Inventor: C. Frederick M. Huntley, East Greenwich, RI (US)

(73) Assignee: KNOA PHARMA LLC, Stamford, CT (US)

( * ) Notice: Subject to any disclaimer, the term of this patent is extended or adjusted under 35 U.S.C. 154(b) by 522 days.

(21) Appl. No.: 18/250,457

(22) PCT Filed: Nov. 2, 2021

(86) PCT No.: PCT/US2021/057737

§ 371 (c)(1),
(2) Date: Apr. 25, 2023

(87) PCT Pub. No.: WO2022/094470

PCT Pub. Date: May 5, 2022

(65) Prior Publication Data

US 2023/0399334 A1 Dec. 14, 2023

Related U.S. Application Data

(60) Provisional application No. 63/108,676, filed on Nov. 2, 2020.

(51) Int. Cl.
*C07D 489/08* (2006.01)

(52) U.S. Cl.
CPC ........ *C07D 489/08* (2013.01); *C07B 2200/13* (2013.01)

(58) Field of Classification Search
CPC .................................................... C07D 489/08
USPC ............................................................ 546/45
See application file for complete search history.

(56) References Cited

U.S. PATENT DOCUMENTS

| | | | |
|---|---|---|---|
| 8,227,609 | B2 | 7/2012 | Weigl et al. |
| 10,316,042 | B2 | 6/2019 | Gebbie et al. |
| 2009/0156815 | A1 | 6/2009 | Wang et al. |
| 2009/0270624 | A1 | 10/2009 | Weigl et al. |
| 2011/0269964 | A1 | 11/2011 | Bao et al. |
| 2018/0008596 | A1 | 1/2018 | Buehler et al. |

FOREIGN PATENT DOCUMENTS

| | | | | |
|---|---|---|---|---|
| EP | 1851226 | A | 11/2007 | |
| JP | 2009528366 | A | 8/2009 | |
| WO | WO-0134608 | A1 | 5/2001 | |
| WO | WO-2007103105 | A2 | 9/2007 | |
| WO | WO-2010136039 | A1 | 12/2010 | |
| WO | WO-2011154826 | A1 | 12/2011 | |
| WO | WO-2016005923 | A1 | 1/2016 | |
| WO | WO 2017-207519 | A1 * | 12/2017 | ........... C07D 489/08 |

OTHER PUBLICATIONS

Healy, J., et al., "Benzylideneoxymorphone: A new lead for development of bifunctional mu/delta opioid receptor ligands," Bioorg. Med. Chem. Lett. 27(3):666-669, Elsevier, Netherlands (Feb. 2017).

Caira, M., et al., "Preparation and crystal characterization of a polymorph, a monohydrate, and an ethyl acetate solvate of the antifungal fluconazole," J. Pharm. Sci. 93(3):601-611, Wiley-Liss, Inc., USA (Mar. 2004).

Van Tonder, E., et al., "Preparation and Physicochemical Characterization of 5 Niclosamide Solvates and 1 Hemisolvate," AAPS PharmSciTech 5(1):Article 12, Available at: http://www.pharmscitech.org (2004).

Bingham, A., et al., "Over one hundred solvates of sulfathiazole," Chem. Commun. 7:603-604, The Royal Society of Chemistry, United Kingdom (Mar. 2001).

Zhang, T., et al., "One-Pot Process for Synthesis of Nalbuphine Hydrochloride and Impurity Control Strategy," Org. Process Res. Dev. 24(9):1707-1717, American Chemical Society, United States (Aug. 2020).

International Search Report and Written Opinion for International Application No. PCT/US2021/057737, European Patent Office, Netherlands, mailed on Feb. 28, 2022, 10 pages.

* cited by examiner

*Primary Examiner* — Charanjit Aulakh
(74) *Attorney, Agent, or Firm* — Sterne, Kessler, Goldstein & Fox P.L.L.C.

(57) ABSTRACT

The application is directed to a process of purifying noroxymorphone by preparing and isolating noroxymorphone bisulfite adduct and regenerating purified noroxymorphone from noroxymorphone bisulfite adduct. The application is also directed to a compound represented by the Formula I, described herein, or a hydrate or zwitterion thereof, and a crystalline form of noroxymorphone bisulfite adduct monohydrate.

16 Claims, 3 Drawing Sheets

PROCESS FOR PURIFYING NOROXYMORPHONE

The present disclosure relates to an improved process for purifying noroxymorphone. Specifically, the present disclosure relates to a process of purifying noroxymorphone via a novel noroxymorphone bisulfite adduct, the noroxymorphone bisulfite adduct, or a hydrate or a zwitterion thereof; and to a process for preparing active pharmaceutical ingredients (APIs), including naloxone, naltrexone, nalmefene, and nalbuphene.

BACKGROUND

Noroxymorphone is an opioid having the following chemical structure:

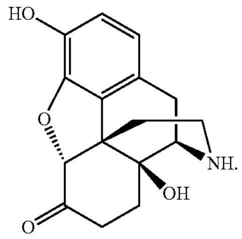 [SMILES: O=C1CC[C@@]2(O)[C@H]3Cc4ccc(O)c5c4[C@@]2(CCN3)[C@H]1O5]

Noroxymorphone is a potent agonist of the μ-opioid receptor, but because of its poor ability to cross the blood-brain-barrier into the central nervous system, it has only minimal analgesic activity. The compound is both a metabolite of oxymorphone and oxycodone.

Noroxymorphone is typically prepared by N-demethylation of oxymorphone as illustrated in Scheme 1:

Scheme 1

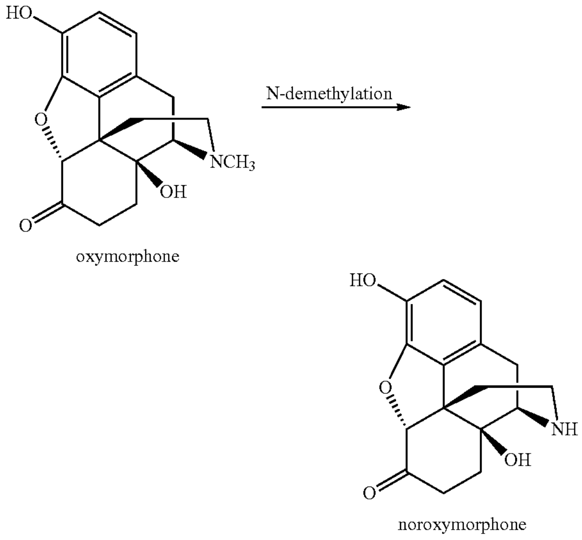

oxymorphone noroxymorphone

Several N-demethylation conditions exist for this transformation. See, e.g., WO 2011/154826 A1, U.S. Pat. No. 8,227,609, and *Bioorg. Med. Chem. Lett,* 2017, 27(3), 666-669.

In most cases, the conditions are harsh, requiring strong acid or base and elevated temperatures. These harsh reaction conditions typically form impurities. The N-demethylation reaction of oxymorphone produces impurities that are typically non-distinct decomposition products. The impurities are difficult to remove and cause the isolated noroxymorphone to be colored. In addition, noroxymorphone has poor solubility properties, making purification of noroxymorphone even more difficult.

Noroxymorphone is typically manufactured specifically as an intermediate in the production of narcotic antagonists, such as naloxone and naltrexone, and other APIs. Naloxone and naltrexone can be prepared from noroxymorphone by alkylation as illustrated in Scheme 2:

Scheme 2

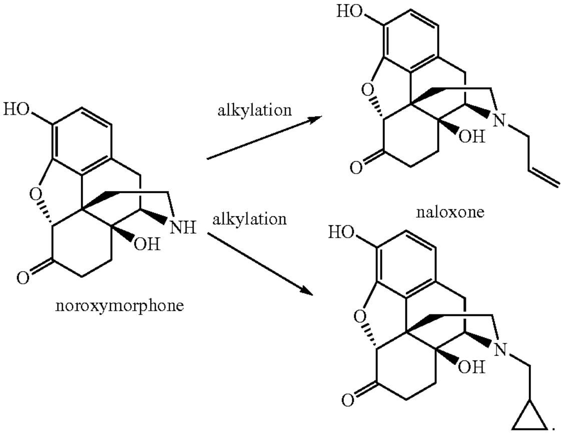

noroxymorphone naloxone naltrexone

Derivatization of noroxymorphone to APIs, such as naloxone and naltrexone, require additional purification and chemical processing steps to remove the impurities carried in with noroxymorphone. The dark, non-distinct impurities are equally challenging to remove from both naltrexone and naloxone. Removal of impurities is necessary to meet color and weight percent assay specifications for the APIs.

The conventional purification method of noroxymorphone involves dissolution in an acid, treatment with decolorizing carbon, filtration, and precipitation of noroxymorphone base from the filtrate by pH adjustment. This method requires large amounts of decolorizing carbon, which is difficult to filter, and which is only partially effective at removing the color and impurities.

Accordingly, there is a need for a purification process for effectively removing impurities from noroxymorphone.

BRIEF SUMMARY OF THE INVENTION

The present disclosure provides an improved process for purifying noroxymorphone. The present disclosure also provides a process for preparing noroxymorphone bisulfite adduct. Noroxymorphone bisulfite adduct is employed in the process for purifying noroxymorphone. In one embodiment, noroxymorphone bisulfite adduct is in a solid form.

An aspect of the present disclosure is directed to a process for preparing noroxymorphone bisulfite adduct. Noroxymorphone bisulfite adduct is an intermediate provided in the process for purifying noroxymorphone of the disclosure.

The process for preparing noroxymorphone bisulfite adduct comprises mixing an aqueous composition comprising noroxymorphone and a source of sulfurous acid; and isolating noroxymorphone bisulfite adduct from the aqueous composition. In some embodiments, the source of sulfurous acid is an aqueous sulfurous acid. In some embodiments, the source of sulfurous acid is sulfur dioxide gas. In some embodiments, the source of sulfurous acid is a bisulfite salt and an acid. In another embodiment, the source of sulfurous acid is a sulfite salt and an acid. In another embodiment, noroxymorphone bisulfite adduct is in a solid form.

In some embodiments, the process for preparing noroxymorphone bisulfite adduct comprises:

- mixing an aqueous composition comprising noroxymorphone and an acid with a bisulfite salt or a sulfite salt to provide noroxymorphone bisulfite adduct; and
- isolating said noroxymorphone bisulfite adduct from the aqueous composition.

In some embodiments, the process for preparing noroxymorphone bisulfite adduct comprises:

- mixing an aqueous composition comprising noroxymorphone and a bisulfite salt or a sulfite salt with an acid to provide noroxymorphone bisulfite adduct; and
- isolating said noroxymorphone bisulfite adduct from the aqueous composition.

In some embodiments, the aqueous composition in the mixing step further comprises an organic co-solvent.

In another aspect, the present disclosure provides noroxymorphone bisulfite adduct prepared by a process of the disclosure.

In another aspect, the present disclosure provides a compound of Formula I:

I

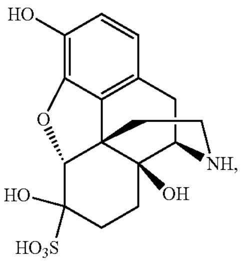

or a hydrate or zwitterion thereof.

In some embodiments, the compound of Formula I is a monohydrate of noroxymorphone bisulfite adduct.

In another aspect, the present disclosure provides a crystalline form of noroxymorphone bisulfite adduct monohydrate. In some embodiments, crystalline Form A of noroxymorphone bisulfite adduct monohydrate is characterized as exhibiting an x-ray powder diffraction (XRPD) pattern having peaks at 11.8±0.2, 13.2±0.2, and 16.7±0.2 degrees two theta when measured by Cu Kα radiation. In some embodiments, crystalline Form A of noroxymorphone bisulfite adduct monohydrate is characterized as exhibiting an XRPD pattern substantially similar to that of FIG. 2.

In some embodiments, noroxymorphone bisulfite adduct monohydrate is in a crystalline form characterized as exhibiting a differential scanning calorimetry thermogram comprising an endotherm with an onset of about 88° C. and with a peak of about 113.5° C.

In some embodiments, noroxymorphone bisulfite adduct monohydrate is in a crystalline form characterized as exhibiting a differential scanning calorimetry thermogram comprising an endotherm with an onset of about 172° C. and with a peak of about 195.5° C.

In another aspect, the present disclosure provides a process for purifying noroxymorphone. The process for purifying noroxymorphone comprises:

- providing an aqueous composition comprising noroxymorphone and one or more colored impurities;
- forming a bisulfite adduct of said noroxymorphone; and
- regenerating purified noroxymorphone from said noroxymorphone bisulfite adduct.

In some embodiments, noroxymorphone bisulfite adduct is formed according to the process for preparing noroxymorphone bisulfite adduct described herein. In some embodiments, noroxymorphone bisulfite adduct formed is in a solid form.

In some embodiments, noroxymorphone to be purified in the aqueous composition is the reaction product of an N-demethylation of oxymorphone.

In some embodiments, the regenerating step is carried out by slurrying noroxymorphone bisulfite adduct in water and adding a base to provide noroxymorphone base. In some embodiments, the base is added gradually until the pH of the slurry is above about 9.5. In some embodiments, the base is an aqueous sodium hydroxide solution. In some embodiments, the base is an aqueous ammonium hydroxide solution. In some embodiments, an organic co-solvent is used in the regeneration step.

In some embodiments, the process for purifying noroxymorphone comprises isolating noroxymorphone base by filtering, slurry-washing in water, and drying to obtain purified noroxymorphone in a solid form.

In another aspect, the present disclosure provides purified noroxymorphone, or a pharmaceutically acceptable salt thereof, prepared by the process of purifying noroxymorphone described herein. In some embodiments, the purified noroxymorphone exhibits an improved colorimetric profile when compared to the colorimetric profile of the original noroxymorphone before purification.

In another aspect, the present disclosure provides a process for the preparation of naloxone, or a pharmaceutically acceptable salt or solvate thereof, wherein said process includes purifying noroxymorphone by a process described herein.

In another aspect, the present disclosure provides a process for the preparation of naltrexone, or a pharmaceutically acceptable salt or solvate thereof, wherein said process includes purifying noroxymorphone by a process described herein.

In another aspect, the present disclosure provides a process for the preparation of nalmefene, or a pharmaceutically acceptable salt or solvate thereof, wherein said process includes purifying noroxymorphone by a process described herein.

In another aspect, the present disclosure provides a process for the preparation of nalbuphene, or a pharmaceutically acceptable salt or solvate thereof, wherein said process includes purifying noroxymorphone by a process described herein.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF THE DRAWINGS/FIGURES

DETAILED DESCRIPTION OF THE INVENTION

Figure 1:
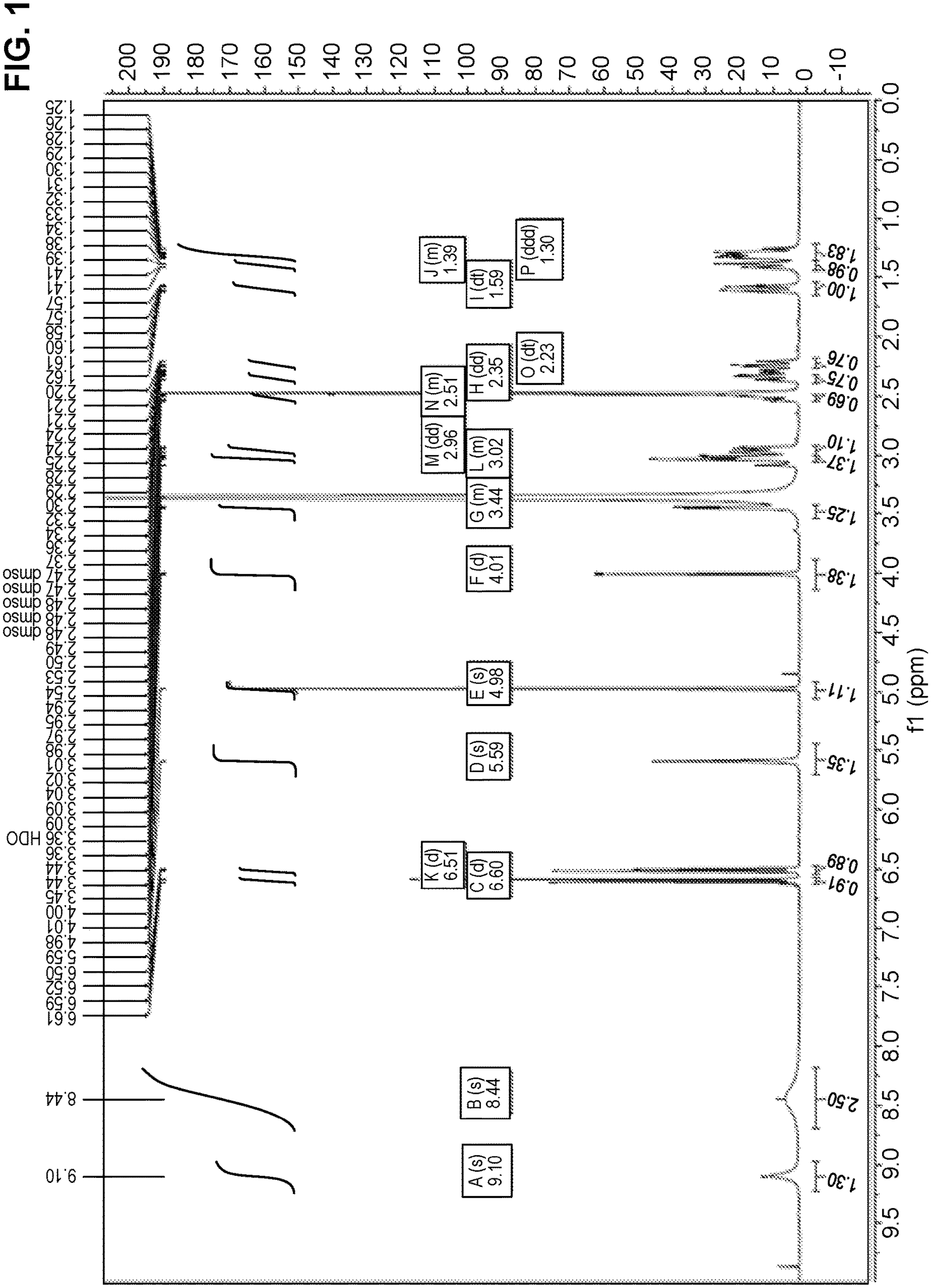
FIG. 1 shows a $^1H$ NMR spectrum for noroxymorphone bisulfite adduct.

The headings provided herein are not limitations of the various aspects of the disclosure, which can be defined by reference to the specification as a whole. It is also to be understood that the terminology used herein is for the purpose of describing particular aspects only, and is not intended to be limiting, since the scope of the present disclosure will be limited only by the appended claims.

Definitions

For convenience, the meaning of some terms and phrases used in the specification, examples, and appended claims are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

The articles “a,” “an,” and “the” are used herein to refer to one or to more than one (i.e., to at least one) of the grammatical object of the article. By way of example, “an element” means one element or more than one element.

As used herein, the term “about” means±10% of the specified value, unless otherwise indicated.

The term “at least” prior to a number or series of numbers is understood to include the number adjacent to the term “at least”, and all subsequent numbers or integers that could logically be included, as clear from context. When at least is present before a series of numbers or a range, it is understood that “at least” can modify each of the numbers in the series or range.

As used herein, the terms “comprises,” “comprising,” “having,” “including,” “containing,” and the like are open-ended terms meaning “including, but not limited to.” To the extent a given embodiment disclosed herein “comprises” certain elements, it should be understood that present disclosure also specifically contemplates and discloses embodiments that “consist essentially of” those elements and that “consist of” those elements.

As used herein the terms “consists essentially of” “consisting essentially of” and the like are to be construed as semi-closed terms, meaning that no other ingredients which materially affect the basic and novel characteristics of an embodiment are included.

As used herein, the terms “consists of,” “consisting of” and the like are to be construed as closed terms, such that an embodiment “consisting of” a particular set of elements excludes any element, step, or ingredient not specified in the embodiment.

As used herein, the term “sulfurous acid” refers to a compound of formula $H_2SO_3$.

As used herein, the term “source of sulfurous acid” refers to a compound or a mixture of two or more compounds that can generate sulfurous acid in an aqueous environment. Sources of sulfurous acid include, for example, aqueous sulfurous acid which is commercially available as a 6% solution in water at Fisher Chemical. Another source of sulfurous acid can be an aqueous mixture of a bisulfite salt with an acid. A source of sulfurous acid can also be sulfur dioxide ($SO_2$) gas in water which provides a bisulfite ion in an aqueous environment. Another source of sulfurous acid can be an aqueous mixture of a sulfite salt and an acid.

The term “bisulfite ion,” as used herein, refers to the hydrogensulfite anion ($HSO_3^-$).

The term “bisulfite salt,” as used herein, refers to any suitable salt that can generate the bisulfite ion in an aqueous environment. Suitable bisulfite salts include alkaline or alkaline earth metal bisulfite salts such as, for example, sodium bisulfite, sodium metabisulfite, potassium bisulfite, potassium metabisulfite, and calcium bisulfite.

The term “sulfite ion,” as used herein, refers to the sulfite anion ($SO_3^{2-}$).

The term “sulfite salt,” as used herein, refers to any suitable salt that can generate the sulfite ion in an aqueous environment. Suitable sulfite salts include alkaline or alkaline earth metal sulfite salts, such as, sodium sulfite, potassium sulfite, and calcium sulfite.

The term “sulfur dioxide gas,” as used herein, refers to $SO_2$ gas.

The term “aqueous composition,” as used herein, refers to an aqueous composition that can be an aqueous solution or an aqueous slurry.

As used herein, the term “solution” refers to a special type of homogeneous mixture composed of only one phase of two or more substances. In such a mixture, a solute is a substance dissolved in another substance, known as a solvent. The solution usually has the state of the solvent when the solvent is the larger fraction of the mixture.

The term “aqueous solution” refers to a solution in which the solvent is water.

As used herein, the term “slurry” is a heterogeneous mixture of solids denser than water suspended in liquid, usually water.

The term “slurrying,” as used herein, refers to the act of converting a solid into a slurry.

As used herein, the term “aqueous slurry” is an aqueous heterogeneous mixture of solids denser than water. An aqueous slurry can contain solid particles and dissolved material.

The term “slurry-washing,” as used herein, refers to purification of the solid from contaminating materials with a solvent, such as water, with minimal dilution.

As used herein, the term “solid” refers to one of the four fundamental states of matter (the others being liquid, gas and plasma). The molecules in a solid are closely packed together and contain the least amount of kinetic energy. A solid is characterized by structural rigidity and resistance to a force applied to the surface. Unlike a liquid, a solid object does not flow to take on the shape of its container, nor does it expand to fill the entire available volume like a gas. The atoms in a solid are bound to each other, either in a regular geometric lattice (crystalline solids), or irregularly (an amorphous solid).

The term “regenerate” or “regeneration,” as used herein, refers to the step of forming noroxymorphone from its bisulfite adduct.

"Hunter Lab color scale" as used herein refers to Hunter L, a, b color scale based on the Opponent-Color Theory. This theory assumes that the receptors in the human eye perceive color as the following pairs of opposites: L scale: light vs. dark, where a low number (0-50) indicates dark and a high number (51-100) indicates light; a scale: red vs. green, where a positive number indicates red and a negative number indicates green; and b scale: yellow vs. blue, where a positive number indicates yellow and a negative number indicates blue. The L value therefore indicates the level of light or dark, the a value redness or greenness, and the b value yellowness or blueness. All three values are required to completely describe an object's color. Accordingly, the higher the L value, the lighter the color of the object.

The phrase "improved colorimetric profile," as used herein, refers to the L, a, and b values from a colorimetric analysis of noroxymorphone obtained from the purification process described herein where compound exhibits a higher L value, a lower a value, and a lower b value when compared to those of the original noroxymorphone before purification.

The "Yellowness Index" or "YI," as used herein, is a number calculated from spectrophotometric data that describes the change in color of a test sample from clear or white to yellow. The higher the YI value, the more yellow is the test sample.

The term "pharmaceutically acceptable salt" refers to a salt prepared from pharmaceutically acceptable inorganic and organic acids. The present disclosure includes all non-toxic pharmaceutically acceptable salts of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like. Exemplary pharmaceutically acceptable acid addition salts include, without limitation, hydrochloric, hydrobromic, hydroiodic, sulfuric, phosphoric, formic, acetic, trifluoroacetic, propionic, citric, and benzoic acid salts.

Acid addition salts can be formed by mixing a solution of a particular compound with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound with a solution of a pharmaceutically acceptable non-toxic base such as sodium hydroxide, potassium hydroxide, lithium hydroxide, choline hydroxide, sodium carbonate and the like.

The term "solvate" as used herein is a combination, physical association and/or solvation of a compound of the present disclosure with a solvent molecule such as, e.g. a disolvate, monosolvate or hemisolvate, where the ratio of solvent molecule to compound of the present invention is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure may be present as solvated forms with a pharmaceutically acceptable solvent, such as water, methanol, ethanol, and the like, and it is intended that the present disclosure includes both solvated and unsolvated forms of compounds of the disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1):Article 12 (2004), and A. L. Bingham et al., *Chem. Commun.:* 603-604 (2001). A typical, non-limiting, process of preparing a solvate would involve dissolving a compound in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate. Some of the compounds disclosed herein may contain one or more asymmetric centers and may thus give rise to enantiomers, diastereomers, and other stereoisomeric forms, such as epimers. The present disclosure is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

The term "polymorph" as used herein refers to a crystalline form of a compound or a salt, hydrate, or solvate thereof, in a particular crystal packing arrangement. All polymorphs have the same elemental composition. The term "crystalline," as used herein, refers to a solid state form which consists of orderly arrangement of structural units. Different crystalline forms of the same compound, or a salt, co-crystal, hydrate, or solvate thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability, and solubility. See, e.g., *Remington's Pharmaceutical Sciences,* $18^{th}$ *ed.*, Mack Publishing, Easton PA, 173 (1990); *The United States Pharmacopeia,* $23^{rd}$ *ed.,* 1843-1844 (1995) (incorporated herein by reference).

Crystalline forms are most commonly characterized by X-ray powder diffraction (XRPD). An XRPD pattern of reflections (peaks, typically expressed in degrees 2-theta) is commonly considered a fingerprint of a particular crystalline form. The relative intensities of the XRPD peaks can widely vary depending on, inter alia, the sample preparation technique, crystal size distribution, filters, the sample mounting procedure, and the particular instrument employed. In some instances, new peaks may be observed, or existing peaks may disappear, depending on the type of instrument or the settings. In some instances, any particular peak in an XRPD pattern may appear as a singlet, doublet, triplet, quartet, or multiplet, depending on the type of instrument or the settings, the sensitivity of the instrument, measuring conditions, and/or purity of the crystalline form. In some instances, any particular peak in an XRPD may appear in a symmetric shape or in an asymmetric shape, e.g., having a shoulder. Moreover, instrument variation and other factors can affect the 2-theta values. A skilled artisan understanding these variations is capable of discriminating or ascertaining the defining features or characteristics of a particular crystal form using XRPD, as well as using other known physicochemical techniques.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral streogenic centers present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The term "alkaline metal" as used herein refers to sodium (Na), potassium (K), and lithium (Li).

The term "alkaline earth metal" as used herein refers to beryllium (Be), magnesium (Mg), calcium (Ca), strontium (Sr), and barium (Ba).

The term "aliphatic alcohol," as used herein, includes Ci-6 alcohols, such as methanol, ethanol, n-propanol, iso-propanol, n-butanol, n-pentanol, and n-hexanol. In some embodiments, the aliphatic alcohol is methanol, ethanol, n-propanol, or iso-propanol.

As used herein, the term "co-solvent" refers to a solvent that in conjunction with another solvent can dissolve a solute.

As used herein, the term "solvent" refers to a liquid substance that dissolves a solute, resulting in a solution. Water is a solvent for polar molecules and the most common solvent used by living things.

The term "organic co-solvent," as used herein, refers to a co-solvent as defined above that is a carbon-based solvent capable of dissolving or dispersing one or more other substances. The organic co-solvent can be a water miscible organic solvent, a water immiscible organic solvent, or a combination thereof. In some embodiments, the organic co-solvent is selected from the group consisting of an aliphatic alcohol, acetonitrile, and tetrahydrofuran (THF), or a combination thereof. In some embodiments, the organic co-solvent is an aliphatic $C_{1-6}$ alcohol, such as, e.g., methanol, ethanol, n-propanol, iso-propanol, n-butanol, n-pentanol, or n-hexanol. In some embodiments, the organic co-solvent is acetonitrile. In some embodiments, the organic co-solvent is THF.

Processes described herein

A number of attempts have been made by the inventor(s) to find a route for effectively purifying noroxymorphone by a process that can be used in a commercial scale, obtaining noroxymorphone with improved purity and colorimetric profile when compared to the original noroxymorphone before purification. It has now been discovered that noroxymorphone can be isolated from an aqueous composition of noroxymorphone and one or more colored impurities in a form of its highly purified bisulfite adduct leaving the one or more colored impurities into the aqueous phase. Crystallization of noroxymorphone as the bisulfite adduct enables noroxymorphone to be separated from dark, non-distinct, tar-like impurities that are commonly present in noroxymorphone. Purified noroxymorphone can then be regenerated from the bisulfite adduct, for example, by treatment with mild base. The purification process described herein is superior to other purification methods for removing such impurities. The process described herein for purifying noroxymorphone is also applicable for large scale and affording purified noroxymorphone in a high yield. The purified noroxymorphone can be further processed to useful APIs, such as naloxone, naltrexone, nalmefene, and nalbuphene, with less downstream purification.

Process for Preparing Noroxymorphone Bisulfite Adduct

The present disclosure provides a process for preparing noroxymorphone bisulfite adduct, said process comprising:

mixing an aqueous composition comprising noroxymorphone and a source of sulfurous acid; and isolating said noroxymorphone bisulfite adduct from the aqueous composition.

In some embodiments, the aqueous composition is an aqueous solution. In some embodiments, the aqueous composition is an aqueous slurry.

The source of sulfurous acid can be any compound or a mixture of two or more compounds that can generate sulfurous acid in an aqueous environment. The compound or mixture of compounds can be a gas, a solid, a liquid, or a mixture thereof.

In some embodiments, the source of sulfurous acid is an aqueous sulfurous acid. Aqueous sulfurous acid is commercially available as a 6% solution in water at, e.g., Fisher Chemical.

In some embodiments, the source of sulfurous acid is sulfur dioxide gas. Sulfur dioxide ($SO_2$) gas in water provides a bisulfite ion ($HSO_3^-$) in an aqueous composition.

In some embodiments, the source of sulfurous acid is a bisulfite salt and an acid.

The bisulfite salt can be any suitable salt that can generate the bisulfite ion in an aqueous environment. In some embodiments, the bisulfite salt is an alkaline or alkaline earth metal bisulfite salt, such as, for example, sodium bisulfite, sodium metabisulfite, potassium bisulfite, potassium metabisulfite, or calcium bisulfite. In some embodiments, the bisulfite salt is an alkaline metal bisulfite salt. In some embodiments, the bisulfite salt is selected from the group consisting of sodium bisulfite, sodium metabisulfite, potassium bisulfite, and potassium metabisulfite. In some embodiments, the bisulfite salt is sodium metabisulfite.

In some embodiments, the source of sulfurous acid is a sulfite salt and an acid.

The sulfite salt can be any suitable salt that can generate the sulfite ion in an aqueous environment. In some embodiments, the sulfite salt is an alkaline or alkaline earth metal sulfite salt, such as, sodium sulfite, potassium sulfite, or calcium sulfite. In some embodiments, the sulfite salt is an alkaline metal sulfite salt. In some embodiments, the sulfite salt is sodium sulfite. In some embodiments, the sulfite salt is potassium sulfite.

The acid present in the source of the sulfurous acid can be an inorganic acid, and organic acid, or a combination thereof. In some embodiments, the acid is an inorganic acid. In some embodiments, the acid is an organic acid. In some embodiments, the acid is a combination of an inorganic acid and an organic acid.

Suitable inorganic acids include, for example, phosphoric acid, hydrochloric acid, and sulfuric acid, and mixtures thereof. In some embodiments, the acid is phosphoric acid. In some embodiments, the acid is a hydrochloric acid. In some embodiments, the acid is sulfuric acid.

Suitable organic acids include, for example, acetic acid, formic acid, propionic acid, and lactic acid, and mixtures thereof. In some embodiments, the organic acid is an acetic acid.

When the source of sulfurous acid is a bisulfite salt and an acid, the mixing in the process of preparing noroxymorphone bisulfite adduct can be carried out several ways. In one embodiment, the mixing is carried out by adding solid bisulfite salt to an aqueous composition comprising noroxymorphone and an acid. In another embodiment, the mixing is carried out by adding an aqueous solution of a bisulfite salt to an aqueous composition comprising noroxymorphone and an acid. In another embodiment, the mixing is carried out by adding an aqueous solution of an acid to an aqueous composition comprising noroxymorphone and a bisulfite salt.

When the source of sulfurous acid is a sulfite salt and an acid, the mixing in the process of preparing noroxymorphone bisulfite adduct can be also carried out several ways. In one embodiment, the mixing is carried out by adding solid sulfite salt to an aqueous composition comprising noroxymorphone and an acid. In another embodiment, the mixing is carried out by adding an aqueous solution of a sulfite salt to an aqueous composition comprising noroxymorphone and an acid. In another embodiment, the mixing is carried out by adding an aqueous solution of an acid to an aqueous composition comprising noroxymorphone and a sulfite salt.

In some embodiments, the sulfurous acid is present in the aqueous composition in an amount to provide a pH of from about 1 to about 6. In some embodiments, the sulfurous acid is present in the aqueous composition in an amount to provide a pH of from about 1 to about 4. In some embodiments, the pH is from about 2.5 to about 3.0. In some embodiments, the pH is about 2.0. In some embodiments, the pH is about 3.0.

In some embodiments, the sulfurous acid is provided gradually within a period of at least about 15 minutes. In some embodiments, the sulfurous acid is provided gradually within a period of at least 15 minutes. In some embodiments, the sulfurous acid is provided gradually within a period of at least 20 minutes. In some embodiments, the sulfurous acid is provided gradually within a period of about 30 minutes.

In some aspects, the process for preparing the bisulfite adduct comprises:

- mixing an aqueous composition comprising noroxymorphone and an acid with a bisulfite salt to provide noroxymorphone bisulfite adduct; and
- isolating noroxymorphone bisulfite adduct from the aqueous composition.

In some aspects, the process for preparing the bisulfite adduct comprises:

- mixing an aqueous composition comprising noroxymorphone and a bisulfite salt with an acid to provide noroxymorphone bisulfite adduct; and
- isolating noroxymorphone bisulfite adduct from the aqueous composition.

In some aspects, the process for preparing the bisulfite adduct comprises:

- mixing an aqueous composition comprising noroxymorphone and an acid with a sulfite salt to provide noroxymorphone bisulfite adduct; and
- isolating noroxymorphone bisulfite adduct from the aqueous composition.

In some aspects, the process for preparing the bisulfite adduct comprises:

- mixing an aqueous composition comprising noroxymorphone and a sulfite salt with an acid to provide noroxymorphone bisulfite adduct; and
- isolating noroxymorphone bisulfite adduct from the aqueous composition.

In some embodiments, noroxymorphone bisulfite adduct is prepared by addition of solid sodium metabisulfite to a mild acidic solution or slurry of noroxymorphone. In some embodiments, noroxymorphone bisulfite adduct is prepared by adding an aqueous solution of sodium metabisulfite to a mild acidic solution of noroxymorphone.

In some embodiments, noroxymorphone bisulfite adduct is prepared by addition of solid sodium sulfite to a mild acidic solution or slurry of noroxymorphone. In some embodiments, noroxymorphone bisulfite adduct is prepared by adding an aqueous solution of sodium sulfite to a mild acidic solution of noroxymorphone.

In some embodiments of these aspects of the disclosure, the pH of the aqueous composition when mixing is from about 1 to about 6. In some embodiments, the pH is from about 1 to about 4. In some embodiments, the pH is from about 2.5 to about 3.0. In some embodiments, the pH is about 2.0. In some embodiments, the pH is about 3.0.

In some embodiments of these aspects of the disclosure, the mixing of the bisulfite (or the sulfite) or the acid, respectively, is carried out gradually within a period of at least about 15 minutes. In some embodiments, the mixing is carried out gradually within a period of at least 15 minutes. In some embodiments, the mixing is carried out gradually within a period of at least 20 minutes. In some embodiments, the mixing is carried out gradually within a period of about 30 minutes.

Noroxymorphone bisulfite adduct can be prepared in water with or without a co-solvent. Suitable co-solvents include any organic co-solvent. In some embodiments, the aqueous composition does not comprise a co-solvent. In some embodiments, the aqueous composition further comprises a co-solvent.

In some embodiments, the aqueous composition further comprises an organic co-solvent. The organic co-solvent can be a water miscible organic solvent, a water immiscible organic solvent, or a combination thereof. In some embodiments, the organic co-solvent is selected from the group consisting of an aliphatic alcohol, acetonitrile, and tetrahydrofuran (THF), or a combination thereof. In some embodiments, the organic co-solvent is an aliphatic $C_{1-6}$ alcohol, such as, e.g., methanol, ethanol, n-propanol, iso-propanol, n-butanol, n-pentanol, or n-hexanol. In some embodiments, the organic co-solvent is acetonitrile. In some embodiments, the organic co-solvent is THF.

The organic co-solvent can be present in the aqueous composition in any ratio with respect to the amount of water present in the composition. In some embodiments, the organic co-solvent is present in the aqueous composition at a ratio of from about 1:100 to about 100:1 v/v with water. In some embodiments, the organic co-solvent is present in the aqueous composition at a ratio of from about 1:70 to about 70:1 v/v with water. In some embodiments, the organic co-solvent is present in the aqueous composition at a ratio of from about 1:50 to about 50:1 v/v with water. In some embodiments, the organic co-solvent is present in the aqueous composition at a ratio of from about 1:30 to about 30:1 v/v with water. In some embodiments, the organic co-solvent is present in the aqueous composition at a ratio of from about 1:20 to about 20:1 v/v with water. In some embodiments, the organic co-solvent is present in the aqueous composition at a ratio of from about 1:10 to about 10:1 v/v with water. In some embodiments, the organic co-solvent is present in the aqueous composition at a ratio of from 1:5 to about 5:1 v/v with water. In some embodiments, the organic co-solvent is present in the aqueous composition at a ratio of about 1:1, 1:2; 1:3, 1:4 or 1:5 v/v with water. In some embodiments, the organic co-solvent is present in the aqueous composition at a ratio of about 2:1, 3:1, 4:1 or 5:1 v/v with water. In some embodiments, the organic co-solvent is present in said aqueous composition at a ratio of about 1:1 v/v with water. In some embodiments, the organic co-solvent present in the aqueous composition is acetonitrile at a ratio of about 1:1 v/v with water.

In some embodiments, the mixing is carried out at a room temperature or at an elevated temperature. In some embodiments, the mixing is carried out at a temperature of about 40° C. to about 90° C. Forming the bisulfite adduct at higher temperatures removes more impurities and color. In some embodiments, noroxymorphone bisulfite adduct is prepared by adding an aqueous solution of sodium metabisulfite at 70° C. over a span of 15 minutes or more.

In some embodiments, the aqueous composition comprising noroxymorphone bisulfite adduct is first allowed to cool to room temperature and then noroxymorphone bisulfite adduct is isolated by filtration. Thus the insoluble bisulfite adduct is separated from the impurities, which remain dissolved. In some embodiments, the process further comprising washing and drying noroxymorphone bisulfite adduct.

In another aspect, the present disclosure provides noroxymorphone bisulfite adduct. The compound can be represented by the following structure of Formula I:

I

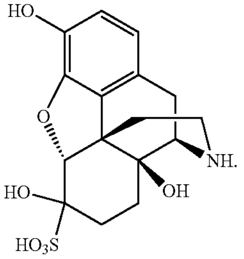

The compound can also be in a zwitterionic form represented by Formula II:

II

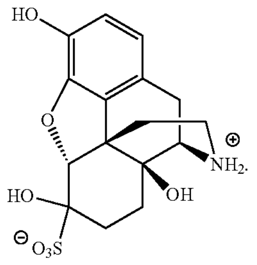

Noroxymorphone bisulfite adduct can be in a form of a solvate, such as a hydrate. In some embodiments, the bisulfite adduct is a monohydrate of noroxymorphone bisulfite adduct.

Figure 2:
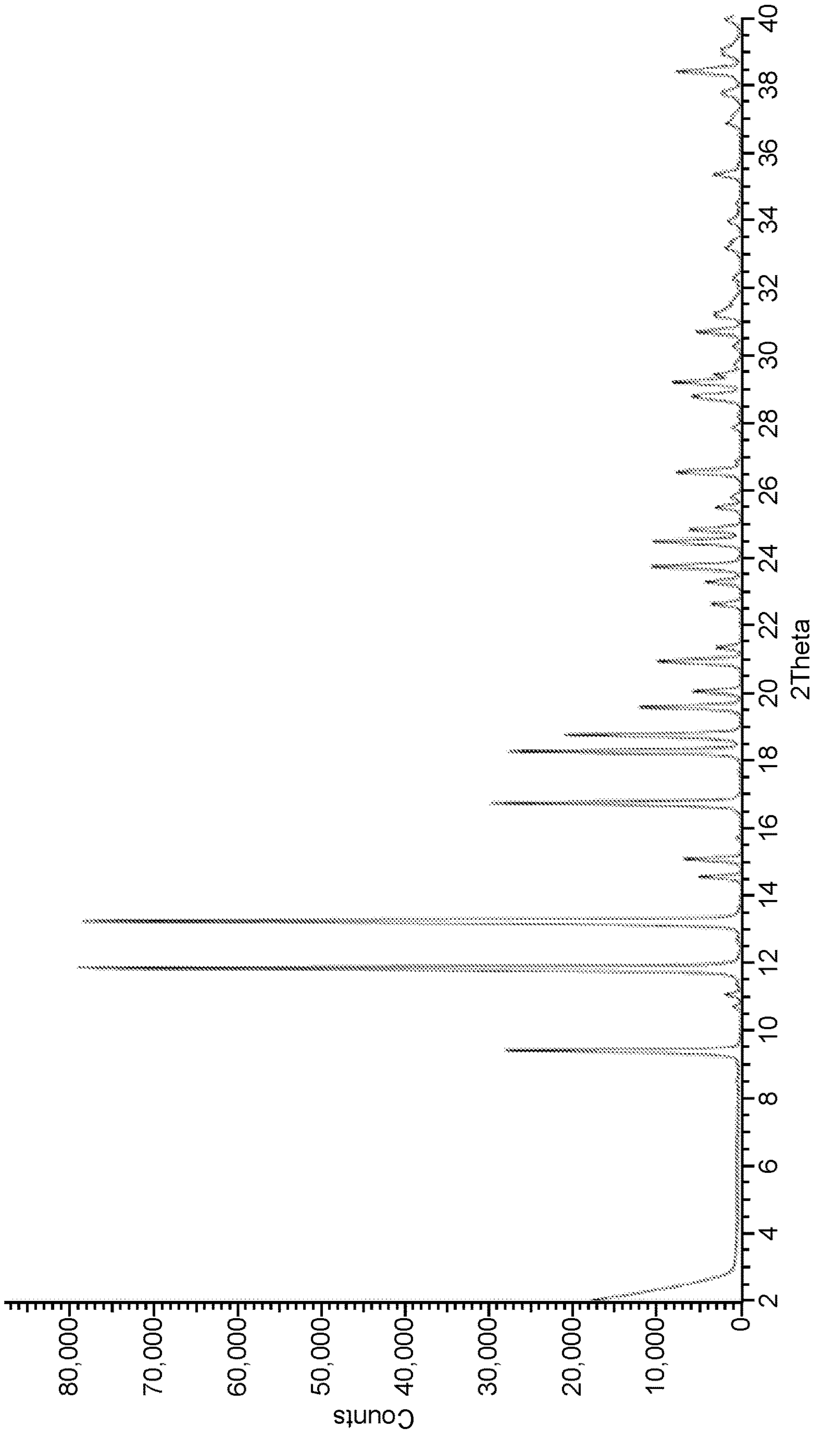
FIG. 2 shows an x-ray powder diffraction (XRPD) pattern for crystalline noroxymorphone bisulfite adduct monohydrate.

In another aspect, the present disclosure provides a crystalline form of noroxymorphone bisulfite adduct monohydrate. An x-ray powder diffraction (XRPD) pattern of the crystalline form of noroxymorphone bisulfite adduct monohydrate is shown in FIG. 2. In some embodiments, crystalline form of noroxymorphone bisulfite adduct monohydrate (hereinafter "crystalline Form A) is characterized by an XRPD pattern substantially as shown in FIG. 2.

In some embodiments, crystalline Form A is characterized by an XRPD pattern having peaks at 11.8±0.2, 13.2±0.2, and 16.7±0.2 degrees two theta when measured by Cu Kα radiation. In another embodiment, crystalline Form A is characterized by an XRPD pattern having peaks at 9.4±0.2, 11.8±0.2, 13.2±0.2, and 16.7±0.2 degrees two theta when measured by Cu Kα radiation. In another embodiment, crystalline Form A is characterized by an XRPD pattern having peaks at 9.4±0.2, 11.8±0.2, 13.2±0.2, 16.7±0.2, and 18.2±0.2 degrees two theta when measured by Cu Kα radiation. In another embodiment, crystalline Form A is characterized by an XRPD pattern having peaks at 9.4±0.2, 11.8±0.2, 13.2±0.2, 16.7±0.2, 18.2±0.2, and 18.7±0.2 degrees two theta when measured by Cu Kα radiation.

In some embodiments, crystalline Form A is characterized by three or more, four or more, five or more, or six or more XRPD peaks listed in the table below with relative intensity>10.0%.

| Index | Angle (°) | d Value (Å) | Relative Intensity |
|---|---|---|---|
| 1 | 9.396 | 9.405 | 34.8% |
| 2 | 11.832 | 7.473 | 100.0% |
| 3 | 13.215 | 6.694 | 98.3% |
| 4 | 16.707 | 5.302 | 37.6% |
| 5 | 18.241 | 4.860 | 34.8% |
| 6 | 18.726 | 4.735 | 26.3% |
| 7 | 19.549 | 4.537 | 15.0% |
| 8 | 20.909 | 4.245 | 12.5% |
| 9 | 23.712 | 3.749 | 13.2% |
| 10 | 24.450 | 3.638 | 13.0% |
| 11 | 29.157 | 3.060 | 10.2% |

Figure 3:
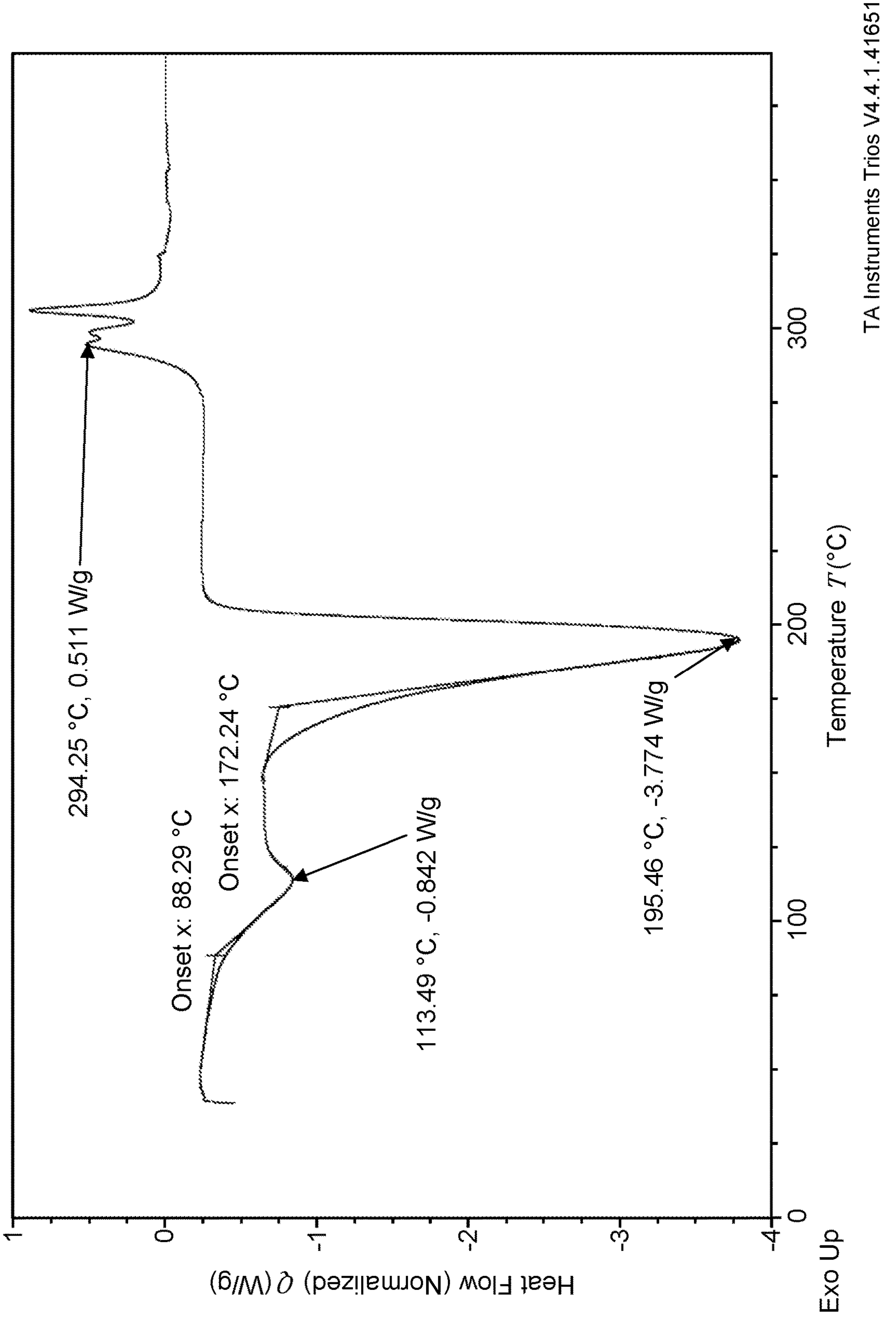
FIG. 3 shows a DSC spectrum of crystalline noroxymorphone bisulfite adduct monohydrate.

The crystalline form of noroxymorphone bisulfite adduct monohydrate can also be characterized by a DSC spectrum shown in FIG. 3. FIG. 3 shows an endotherm with an onset of about 88° C. and with a peak of about 113.5° C. FIG. 3 also shows an endotherm with an onset of about 172° C. and with a peak of about 195.5° C.

Process for Purifying Noroxymorphone

In another aspect, the present disclosure provides a process for purifying noroxymorphone. The process comprises:

providing an aqueous composition comprising noroxymorphone and one or more colored impurities;

forming a bisulfite adduct of the noroxymorphone; and regenerating purified noroxymorphone from the noroxymorphone bisulfite adduct.

In some embodiments, the bisulfite adduct is formed according to the process described above for preparing noroxymorphone bisulfite adduct.

In some embodiments, noroxymorphone starting material in the aqueous composition is the reaction product of an N-demethylation of oxymorphone. The N-methylation of oxymorphone can be carried out as described in, e.g., WO 2011/154826 A1, U.S. Pat. No. 8,227,609, and *Bioorg. Med. Chem. Lett*, 2017 27(3), 666-669.

Oxymorphone can be prepared, for example, starting from an oxidation reaction of oripavine followed by hydrogenation as described in, e.g., U.S. Pat. No. 10,316,042.

The bisulfite adduct of noroxymorphone can easily be converted back to noroxymorphone through a slurry-to-slurry transformation using mild aqueous base, thus affording purified noroxymorphone. In some embodiments, the regeneration of noroxymorphone is carried out by slurrying noroxymorphone bisulfite adduct in water and adding a base to provide noroxymorphone base. In some embodiments, the base is added gradually until the pH of the slurry is above about 9.5. In some embodiments, the base is added gradually over at least 15 minutes. In some embodiments, the base is added gradually over at least 20 minutes. In some embodiments, the base is added gradually over at least 30 minutes.

A hydroxide, alkoxide, or carbonate base can be used in the regeneration of noroxymorphone from the bisulfite adduct. In some embodiments, the base is an aqueous sodium hydroxide solution. In some embodiments, the base is an aqueous ammonium hydroxide solution.

The regeneration is carried out at a room temperature or at an elevated temperature. In some embodiments, the regeneration is carried out at room temperature. In some embodiments, the regeneration is carried out at a temperature of about 60° C. to about 75° C.

In some embodiments, an organic co-solvent is used in the regeneration of noroxymorphone. Suitable organic co-solvents include those described above in connection with the process of preparing noroxymorphone bisulfite adduct.

The regeneration further comprises isolating noroxymorphone base by filtering, slurry-washing in water, and drying to obtain purified noroxymorphone in a solid form. The resulting purified noroxymorphone has higher HPLC weight% assay, HPLC area% purity, and lighter color.

An example of the process for purifying noroxymorphone as described herein is presented in Scheme 3 below:

Scheme 3

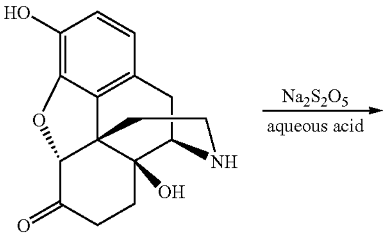

noroxymorphone

-continued

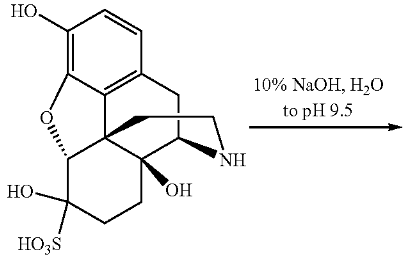

noroxymorphone bisulfite adduct

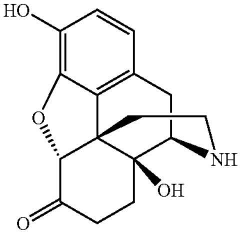

purified noroxymorphone

In another aspect, the present disclosure provides a purified noroxymorphone prepared by the process described herein, or a pharmaceutically acceptable salt thereof, wherein the purified noroxymorphone exhibits an improved colorimetric profile when compared to the colorimetric profile of the original noroxymorphone before purification.

In another aspect, the present disclosure provides a process for the preparation of naloxone, or a pharmaceutically acceptable salt or solvate thereof, wherein the process includes purifying noroxymorphone by a process described herein.

In another aspect, the present disclosure provides a process for the preparation of naltrexone, or a pharmaceutically acceptable salt or solvate thereof, wherein the process includes purifying noroxymorphone by a process as described herein.

Naloxone and naltrexone, and their pharmaceutically acceptable salts and solvates thereof, can be prepared from the purified noroxymorphone described herein, for example, as described in WO 2016/005923, IN2012MU00409, and US 2011/0269964 A1.

In another aspect, the present disclosure provides a process for the preparation of nalmefene, or a pharmaceutically acceptable salt or solvate thereof, wherein the process includes purifying noroxymorphone by a process as described herein. Nalmefene and its pharmaceutically acceptable salts can be prepared from the purified noroxymorphone described herein, for example, as described in WO 2010/136039 Al.

In another aspect, the present disclosure provides a process for the preparation of nalbuphene, or a pharmaceutically acceptable salt or solvate thereof, wherein the process includes purifying noroxymorphone by a process as described herein. Nalbuphene and its pharmaceutically acceptable salts can be prepared from the purified noroxymorphone described herein, for example, as described in *Org. Proc. Res. Dev.*, 2020, 24(9), 1707-17.

EXAMPLES

The method of treatment described herein is now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

Noroxymorphone Colorimetry Determination Method

The colorimetry analysis of noroxymorphone starting materials and purified products was conducted as follows: An about 300 mg portion of noroxymorphone was dried in a vacuum drying oven at 105° C. for three hours and cooled in a vacuum desiccator. The dried solids were dissolved in 1.0 M phosphoric acid (125±2 mg noroxymorphone in 25 mL using a volumetric flask). The solution was analyzed on a Hunterlab Ultra Scan VIS colorimeter, with a standard of 1.0 M phosphoric acid, in a 25 mL quartz cell (10 mm length). The colorimetry data was processed using Easy-match QC software version 4.86.03.

The results of the colorimetry analysis are presented with Hunter Lab color scale values L, a, and b, and yellowness index (YI).

HPLC Analysis

Chromatographic Conditions:

- Mobile phase A: 25 mM Potassium Phosphate Buffer (pH 8.30)/MeOET (90/10 v/v)
- Mobile phase B: 25 mM Potassium Phosphate Buffer (pH 8.30)/MeOff (25/75 v/v)

Gradient Conditions:

| | Time | Flow | % A | %8 | Curve |
|---|---|---|---|---|---|
| 1 | 0 | 1.0 | 100 | 0 | 6 |
| 2 | 5 | 1.0 | 100 | 0 | 6 |
| 3 | 45 | 1.0 | 0 | 100 | 6 |
| 4 | 46 | 1.0 | 100 | 0 | 6 |
| 5 | 50 | 1.0 | 100 | 0 | 6 |

- Detection: UV 225 nm
- Column: Phenomenex Gemini 5 μ 250×4.6 mm, Cat# 00G-4435-E0, or equivalent
- Injection volume: 10 μL
- Flow rate: 1.0 ml/min
- Column temperature: 40° C.
- Run thine: 50 min
- Needle Wash: 50% Methanol in Water
- HPLC area % purity is calculated using the following equation:

$$\text{Assay (\% Area)} = \frac{A_{NHM}}{\sum Ai} \times 100$$

where:

- Assay (% Area)=% area of noroxymorphone;
- $A_{NHM}$=Peak area response of noroxymorphone peak form sample;
- $A_i$=sum of the areas of all peaks for sample; and
- 100=conversion factor for percentage.
- HPLC weight % assay is calculated using the following equation:

$$\text{\% Purity (as is)} = \frac{Rs \times Wstd \times 100}{Rstd \times Ws},$$

where

- Rs=peak responses of noroxymorphone for sample;
- Rstd=average peak responses of noroxymorphone peaks for all bracketing standard injections;
- Wstd=weight of standard, corrected for purity, mg;
- Ws=weight of sample, mg; 100=conversion factor for percentage.

Example 1

Preparation of Crude Noroxymorphone and Purification by Treating with Decolorizing Carbon Followed by Hydrogenation Crude noroxymorphone was prepared by the following procedure: Crude oxymorphone was suspended in approximately seven volumes of tert-amyl alcohol and treated with sodium iodide and sodium bicarbonate. The mixture was heated to reflux and distilled to approximately one-half volume to remove residual moisture. The resulting mixture was then treated with ethyl chloroformate at approximately 80° C. to provide the 3,17-diethoxycarbonylnoroxymorphone. After basic hydrolysis of the carbonate, the mixture was acidified and washed. The tert-amyl alcohol was displaced with water via distillation and the mixture was treated with aqueous sulfuric acid to effect hydrolysis of the carbamate. After pH adjustment, crude noroxymorphone was isolated as a precipitate.

Crude noroxymorphone was treated by decolorizing carbon and hydrogenation to obtain low ABUK (i.e., a,(α,β unsaturated ketone) noroxymorphone by the following procedure: Crude noroxymorphone was dissolved in approximately five volumes of water containing approximately 2.4 equivalents of phosphoric acid and approximately 25% by weight of activated carbon. The solution was heated to approximately 90° C. and held for several hours. After cooling, the carbon was removed by filtration. The filter cake was washed with approximately two volumes of water and the combined filtrates are treated with 5% palladium on carbon under 75 psia of hydrogen at approximately 80° C. Upon reaction completion, the mixture was cooled and the catalyst removed by filtration. After pH adjustment, the precipitated low ABUK noroxymorphone was isolated by filtration.

Example 2

Providing Purified Noroxymorphone from low ABUK Noroxymorphone

Low ABUK noroxymorphone (containing 11.2% water, 50.02 g as-is, 44.42 g corrected for water content, 154.6 mmol) prepared in Example 1 was slurried in water:MeCN (1:1, v:v, 250 mL). Phosphoric acid (85%, 15 mL) was added to a pH of 2.9, where complete dissolution was observed. Sodium metabisulfite (29.4 g, 1 eq, 2 molar equivalents of sodium bisulfite) was added as a solution in water (60 mL) at a temperature of 70° C. within 30 minutes. The reaction mixture was allowed to cool to room temperature. The solids were filtered and slurry-washed in water: MeCN (1:1, v:v, 80 mL).

The wet cake bisulfite adduct (64.73 g) was slurried in water (200 mL). Sodium hydroxide (10 wt % solution, ~100 mL) was added dropwise over 20 minutes. The pH during the addition was about 8.5. At the end, the pH increased precipitously to 10.5. The mixture was stirred for 1 hour, and the pH back-buffered to 8.4. A few drops of base were added to a final pH of 10.16. The mixture was filtered, and the solids were slurry-washed with water (80 mL) and dried in a vacuum drying oven at 70° C. for 16 h. The solids were allowed to equilibrate open to the air to a constant weight to provide the product, purified noroxymorphone (42.13 g, 1.34% water by KF, 94% yield after correcting for water).

Example 3

Providing Purified Noroxymorphone from Crude Noroxymorphone

Crude noroxymorphone (containing 38.3% water, 61.97 g as-is, 44.42 g corrected for water content, 154.6 mmol) prepared in Example 1 was slurried in water:MeCN (1:1, v:v, 250 mL). Phosphoric acid (85%, 15 mL) was added to a pH of 2.9, where complete dissolution was observed. Sodium metabisulfite (29.4 g, 1 eq, 2 molar equivalents of sodium bisulfite) was added as a solution in water (60 mL) at a temperature of 70° C. within 30 minutes. The reaction mixture was allowed to cool to room temperature. The solids were filtered and slurry-washed in water:MeCN (1:1, v:v, 80 mL).

The wet cake bisulfite adduct (57.12 g) was slurried in water (200 mL). Sodium hydroxide (10 wt % solution, ~80 mL) was added dropwise over 20 minutes. The pH during the addition was about 8.5. At the end, the pH increased precipitously to 10.2. The mixture was stirred for 1 hour, and the pH back-buffered to 9.3. The mixture was filtered, and the solids were slurry-washed with water (80 mL) and dried in a vacuum drying oven at 70° C. for 16 h. The solids were allowed to equilibrate open to the air to a constant weight (35.35 g, 6.46% water by KF, 79% yield after correcting for water).

Example 4

HPLC and Color Analysis of the Starting Materials and Purified Noroxymorphone from Examples 2 and 3

A portion of each of the starting materials and products from Example 2 and Example 3 were dried in a vacuum drying oven at 105° C. for three hours and cooled in a vacuum desiccator.

HPLC analysis: The dried solids were analyzed for HPLC weight percent assay and purity (100±2 mg in 50 mL 0.085% phosphoric acid). The results are presented below in Table 1:

TABLE 1

| Sample | HPLC wt % assay (dried basis) | HPLC area % purity |
|---|---|---|
| Example 2 | | |
| Example 2 starting material | 99.74 | 99.13 |
| Example 2 product | 102.89 | 99.38 |
| Example 3 | | |
| Example 3 starting material | 91.33 | 97.53 |
| Example 3 product | 99.19 | 99.33 |

In both Examples 2 and 3, the weight % assay and area % purity increased in the material purified according to the process of the disclosure through the bisulfite adduct.

Colorimetry analysis: The dried solids were analyzed for color (125±2 mg in 25 mL 1M phosphoric acid). The results are presented below in Table 2:

TABLE 2

| Sample | L | a | b | Yellowness index (YI) |
|---|---|---|---|---|
| Example 2 | | | | |
| Example 2 starting material | 95.19 | 0.16 | 14.04 | 25.29 |
| Example 2 product | 99.00 | −0.02 | 2.51 | 4.60 |
| Example 3 | | | | |
| Example 3 starting material | 64.83 | 16.33 | 56.03 | 115.17 |
| Example 3 product | 72.25 | 10.34 | 42.11 | 87.04 |

In both Examples 2 and 3, the color was improved by purification according to the process of the disclosure through the bisulfite adduct.

Example 5

Purification of Noroxymorphone: Noroxymorphone Bisulfite Adduct Prepared in a Mixture Comprising Water, THF, and Sulfurous Acid Crude noroxymorphone (containing 38.3% water, 12.39 g as-is, 8.88 g corrected for water content, 30.9 mmol) prepared in Example 1 was slurried in THF (62 mL) and heated to 63° C. Sulfurous acid (6 wt % $SO_2$ in water, 1.1 eq, 64 mL) was added dropwise over 20 min. The pH was 2.69 at 60° C. The slurry was allowed to cool to 25° C., and the solids were filtered. The solids were slurried in water/THF (1:1, 20 mL) and heated to 63° C. for one hour, cooled to room temperature, and filtered.

The wet cake bisulfite adduct was slurried in water (40 mL) and heated to 65° C. Sodium hydroxide (10 wt % solution, ~18 mL) was added dropwise over 20 minutes. The pH during the addition was about 7.5. At the end, the pH increased precipitously to 8.9. The reaction was allowed to cool to room temperature. The pH of the mixture was adjusted from 9.9 to 10.2 with a few more drops of base. The slurry was stirred for 1 hour. The mixture was filtered, and the solids were slurry-washed with water (20 mL) and dried in a vacuum drying oven at 70° C. for 16 h. The solids were allowed to equilibrate open to the air to a constant weight to obtain the product, purified noroxymorphone (7.10 g, 0.96% water by KF, 79% yield after correcting for water).

Colorimetry analysis: An about 300 mg portion of each of the starting material and the product were dried in a vacuum drying oven at 105° C. for three hours and cooled in a vacuum desiccator. The dried solids were analyzed for color (125±2 mg in 25 mL 1M phosphoric acid). The results are presented in Table 3 below:

TABLE 3

| Sample | L | a | b | YI |
|---|---|---|---|---|
| Example 5 starting material | 64.83 | 16.33 | 56.03 | 115.17 |
| Example 5 product | 80.97 | 4.57 | 26.87 | 54.53 |

Example 6

Purification of Noroxymorphone: Noroxymorphone Bisulfite Adduct Prepared in a Mixture Comprising Water, THF, and Sulfur Dioxide Gas Low-ABUK noroxymorphone (11.22% water, 50.56 g, 44.89 g corrected for water content, 156.2 mmol) prepared in Example 1 was slurried in THF/water (1:1 v/v, 250 mL). The pH was 7.77. Sulfur dioxide gas (29.94 g, 467 mmol, 3.0 eq) was added over 14 minutes, to a final pH of 1.89. After stirring for 50 minutes at room temperature, the solids were filtered, and then re-heated in THF/water (1:1, v/v, 90 mL) for one hour. After cooling to room temperature, the solids were filtered to obtain noroxymorphone bisulfite adduct. The bisulfite adduct was slurried in water (150 mL) and heated to 70° C. Ammonium hydroxide (92 mL) was added to a pH of 9.4 (at 65° C.). The mixture was cooled to room temperature, and the pH was 10.4. The solids were filtered, slurry-washed in water/$NH_4OH$ (90 mL, 19:1), and dried in a 70° C. vacuum drying oven overnight. The solids were allowed to equilibrate open to the air for one day to obtain the product, purified noroxymorphone (46.67 g, 11.22% water, 41.43 g corrected for water, 92% yield).

HPLC and colorimetry analysis: A sample (300 mg) of the starting material and the product were dried in a 105° C. vacuum drying oven for three hours and cooled in a desiccator. The dried noroxymorphone samples were analyzed for weight percent assay (100 mg in 50 mL 0.085% $H_3PO_4$) and the results are presented in Table 4:

TABLE 4

| Sample | Wt % assay (dried basis) | HPLC area % |
|---|---|---|
| Example 6 starting material | 99.17 | 98.64 |
| Example 6 product | 100.82 | 99.26 |

The same dried samples were also analyzed for color (125 mg in 25 mL 1 N $H_3PO_4$) and the results are presented in Table 5:

TABLE 5

| Sample | L | a | b | YI |
|---|---|---|---|---|
| Example 6 starting material | 91.38 | 0.15 | 13.91 | 25.89 |
| Example 6 product | 94.64 | −0.30 | 4.51 | 8.31 |

Example 7

Purification of Noroxymorphone: Noroxymorphone Bisulfite Adduct Prepared Using an Organic Acid Crude noroxymorphone (38.3% water, 12.39 g, 8.88 g corrected for water content, 30.9 mmol) prepared in Example 1 was slurried in THF/water (1:1 v/v, 50 mL). Acetic acid (glacial, 5 mL) was added to a final pH of 5.5. The resulting solution was heated to 62° C., and sodium metabisulfite (33 wt % solution in water, 17.64 g, 30.9 mmol, 2 eq of sodium bisulfite) was added dropwise over 20 minutes. Solids began forming two minutes in to the addition. After cooling to room temperature, the solids were filtered. The solids were slurry washed in THF/water (20 mL) for one hour at 62° C., cooled, and filtered to obtain noroxymorphone bisulfite adduct. The bisulfite adduct was slurried in water (40 mL) and heated to 70° C. Ammonium hydroxide (20 mL) was added to a pH of 9.4 (at 65° C.). The mixture was cooled to room temperature, and the solids were filtered, slurry-washed in water/$NH_4OH$ (20 mL, 19:1), and dried in a 70° C. vacuum drying oven overnight. The solids were allowed to equilibrate open to the air for one day to obtain the product, purified noroxymorphone (7.09 g, 0.62% water, 80% yield).

Colorimetry analysis: A sample (200 mg) of both the starting material and the product were dried in a 105° C. vacuum drying oven for three hours and cooled in a desiccator. The dried noroxymorphone samples were analyzed for color (125 mg in 25 mL 1 N $H_3PO_4$) and the results are presented in Table 6.

TABLE 6

| Sample | L | a | b | YI |
|---|---|---|---|---|
| Example 7 starting material | 59.45 | 15.84 | 53.02 | 116.65 |
| Example 7 product | 77.82 | 4.52 | 23.68 | 50.82 |

Example 8

Purification of Noroxymorphone: Noroxymorphone Bisulfite Adduct Prepared by Adding Sodium Metabisulfite as a Solid Low ABUK noroxymorphone (15.32 g, 12.25% water, 46.8 mmol) prepared in Example 1 was slurried in water (100 mL) and acidified to pH 1.2 with conc. HCl (about 6 mL). The resulting slurry was stirred for 10 min, and then sodium metabisulfite (8.90 g, 1.0 eq, 2.0 molar equivalents bisulfite) was added in one portion. The slurry darkened from a light tan to a yellow color. The pH increased to 2.30. After stirring for one hour, the yellow solids were filtered and slurry-washed with water (50 mL).

The wet cake bisulfite adduct was slurried in water (100 mL). Sodium hydroxide (10 wt % solution, 33 mL) was added dropwise over 20 minutes. The pH during the addition was about 8.5. At the end, the pH increased suddenly to 10.5. The mixture was stirred for minutes, and then the pH was lowered with 1 N HCl (5 drops) to pH 9.5. The mixture was filtered, and the solids were slurry-washed with water (50 mL) and dried in a 70° C. in a vacuum drying oven for five hours to obtain the product, noroxymorphone (14.98 g, 13.8% water by KF, 96% yield after correcting for water).

Example 9

Example from Preparing the Bisulfite Adduct by Adding Acid to a Mixture of Noroxymorphone, Sodium Bisulfite, and Solvent Crude noroxymorphone (38.3% water, 12.39 g, 8.88 g corrected for water content, mmol) prepared in Example 1 was slurried in THF (25 mL), water (15 mL), and a 33 wt % solution of sodium metabisulfite in water (17.64 g, 30.9 mmol, 2 eq of sodium bisulfite). The slurry was heated to 62° C. and phosphoric acid (75%, 6 mL) was added dropwise to a pH of 3.0 (at 64° C.). After cooling to room temperature, the solids were filtered. The solids were slurry washed in THF/water (20 mL) for one hour at 62° C., cooled, and filtered. The bisulfite adduct was slurried in water (40 mL) and heated to 70° C. Ammonium hydroxide (20 mL) was added to a pH of 9.4 (at 65° C.). The mixture was cooled to room temperature, and the solids were filtered, slurry-washed in water/$NH_4OH$ (20 mL, 19:1), and dried in a 70° C. vacuum drying oven overnight. The solids were allowed to equilibrate open to the air for one day to obtain the product, noroxymorphone (6.92 g corrected for water, 1.74% water, 78% yield).

Colorimetric analysis: A sample (200 mg) of both the starting material and the product were dried in a 105° C. vacuum drying oven for three hours and cooled in a desiccator. The dried noroxymorphone samples were analyzed for color (125 mg in 25 mL 1 N $H_3PO_4$) and the results are presented in Table 7:

TABLE 7

| Sample | L | a | b | YI |
|---|---|---|---|---|
| Example 9 starting material | 59.45 | 15.84 | 53.02 | 116.65 |
| Example 9 product | 77.89 | 5.02 | 28.67 | 59.29 |

Example 10

Characterization of Noroxymorphone Bisulfite Adduct

Characterization by $^1H$ NMR: The structure of noroxymorphone bisulfite adduct including proton numbering is presented below:

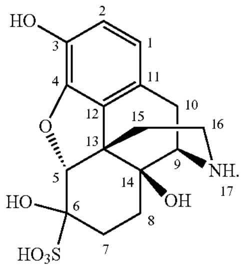

The $^1H$ NMR spectrum is provided in FIG. 1. The bisulfite adduct can form two diastereomers, differing at position 6. Upon dissolution in DMSO $d_6$, the $^1H$ NMR shows primarily a single diastereomer. Over time, the $^1H$ NMR shows what is believed to be racemization at this stereocenter, which generates a mixture of two diastereomers.

TABLE 8

$^1H$ NMR Proton Assignments for noroxymorphone bisulfite adduct as primarily a single diastereomer

| δ (ppm)[a] | Multiplicity | J value (Hz) | # of Protons | Classification (Position) |
|---|---|---|---|---|
| 9.10 | S | n/a | 1 | Exchangeable |
| 8.44 | s | n/a | 2 | Exchangeable |
| 6.60 | d | 8.1 | 1 | 2 |
| 6.51 | d | 8.1 | 1 | 1 |
| 5.59 | S | n/a | 1 | Exchangeable |
| 4.98 | S | n/a | 1 | 5 |
| 4.01 | D | 1.8 | 1 | Exchangeable |
| 3.54-3.43 | M | n/a | 1 | 9 |
| 3.06-3.00 | M | n/a | 2 | 10a, 10b |
| 2.96 | Dd | 13.1, 4.5 | 1 | 16a |
| 2.51 | m | n/a | 1 | 16b |
| 2.35 | Dd | 13.1, 4.9 | 1 | 15a |
| 2.23 | Dt | 13.8, 2.7 | 1 | 8a |
| 1.59 | Dt | 14.2, 3.3 | 1 | 8b |
| 1.44-1.36 | M | n/a | 2 | 7a, 15b |
| 1.30 | ddd | 16.4, 11.4, 7.7 | 1 | 7b |

[a]14 mg/mL noroxymorphone bisulfite adduct in DMSO-d6, 400 MHz, 16 scans.

All proton NMR signals were found to be consistent with the structure of noroxymorphone bisulfite provided in FIG. 1.

Characterization by XRPD: crystalline Form A of noroxymorphone bisulfite adduct monohydrate has the XRPD pattern as shown in FIG. 2. The XRPD 2-theta maxima values are presented in Table 9 below for the peaks with NLT 10% relative intensity.

TABLE 9

XRPD 2-theta maxima values for crystalline Form A of noroxymorphone bisulfite adduct monohydrate with relative intensity >10.0%

| Index | Angle (°) | d Value (Å) | Relative Intensity |
|---|---|---|---|
| 1 | 9.396 | 9.405 | 34.8% |
| 2 | 11.832 | 7.473 | 100.0% |
| 3 | 13.215 | 6.694 | 98.3% |
| 4 | 16.707 | 5.302 | 37.6% |
| 5 | 18.241 | 4.860 | 34.8% |
| 6 | 18.726 | 4.735 | 26.3% |
| 7 | 19.549 | 4.537 | 15.0% |
| 8 | 20.909 | 4.245 | 12.5% |
| 9 | 23.712 | 3.749 | 13.2% |
| 10 | 24.450 | 3.638 | 13.0% |
| 11 | 29.157 | 3.060 | 10.2% |

Characterization by DSC: Crystalline Form A of noroxymorphone bisulfite adduct monohydrate has the following DSC heat flow minima shown in FIG. 3. The DSC (10° C./min to 400° C.) of the crystalline form of noroxymorphone bisulfite adduct monohydrate has two endotherms, whose onset temperatures and heat flow minima are summarized in below in Table 10:

TABLE 10

DSC Data Summary of crystalline Form A of noroxymorphone bisulfite adduct monohydrate

| | Onset temp | Heat flow minimum |
|---|---|---|
| Endotherm 1 | 88.3° C. | 113.5° C. |
| Endotherm 2 | 172.2° C. | 195.5° C. |

Having now fully described this disclosure, it will be understood by those of ordinary skill in the art that the same can be performed within a wide and equivalent range of conditions, formulations, and other parameters without affecting the scope of the invention or any embodiment thereof.

Other embodiments of the disclosure will be apparent to those skilled in the art from consideration of the specification and practice of the invention disclosed herein. It is intended that the specification be considered exemplary only, with a true scope and spirit of the invention being indicated by the following claims.

All patents, patent applications, and publications cited herein are fully incorporated by reference herein in their entirety.

What is claimed is:

1. A process for purifying noroxymorphone, said process comprising:

providing an aqueous composition comprising noroxymorphone and one or more colored impurities;

forming a noroxymorphone bisulfite adduct represented by Formula I (Formula I)

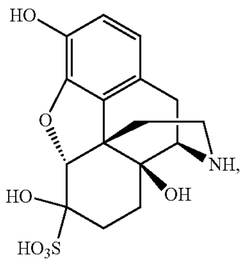

or a hydrate or zwitterion thereof, wherein said forming comprises mixing an aqueous composition comprising noroxymorphone and a source of sulfurous acid to provide said noroxymorphone bisulfite adduct;

isolating the noroxymorphone bisulfite adduct from the aqueous composition; and regenerating purified noroxymorphone from said noroxymorphone bisulfite adduct.

2. The process of claim 1, wherein said mixing is performed by adding solid bisulfite salt to the aqueous composition comprising noroxymorphone and a source of sulfurous acid; or adding an aqueous solution of the bisulfite salt to the aqueous composition comprising noroxymorphone and a source of sulfurous acid; or adding an aqueous solution of the sulfurous acid to the aqueous composition comprising noroxymorphone and the bisulfite salt.

3. The process of claim 1, wherein said regenerating is carried out by slurrying said noroxymorphone bisulfite adduct in water and adding a base to provide a noroxymorphone base.

4. The process of claim 1, wherein the sulfurous acid is present in the aqueous composition in an amount to provide a pH of from about 1 to about 6.

5. The process of claim 4, wherein the pH is from about 2.5 to about 3.0.

6. The process of claim 1, wherein the source of sulfurous acid is a bisulfite salt and an acid.

7. The process of claim 6, wherein the bisulfite salt is selected from the group consisting of sodium bisulfite, sodium metabisulfite, potassium bisulfite, and potassium metabisulfite.

8. The process of claim 1, wherein the aqueous composition further comprises an organic co-solvent.

9. The process of claim 8, wherein the organic co-solvent is selected from the group consisting of an aliphatic alcohol, acetonitrile, tetrahydrofuran, and combinations thereof.

10. The process of claim 8, wherein the organic co-solvent is present in the aqueous composition at a ratio of about 1:1 (v/v) with water.

11. The process of claim 1, wherein the mixing is carried out at an elevated temperature.

12. The process of claim 11, wherein the mixing is carried out at a temperature of about 40° C. to about 90° C.

13. The process of claim 1, wherein the aqueous composition comprising the noroxymorphone bisulfite adduct is allowed to cool to room temperature before the noroxymorphone bisulfite adduct is isolated by filtration.

14. The process of claim 3, wherein the base is added gradually until the pH of the slurry is above about 9.5.

15. The process of claim 3, wherein the base is an aqueous sodium hydroxide solution or an aqueous ammonium hydroxide solution.

16. The process of claim 1, wherein the source of sulfurous acid is aqueous sulfurous acid, sulfur dioxide gas, a bisulfite salt and an acid, or a sulfite salt and an acid.

* * * * *